United States Patent [19]

McComsey et al.

[11] 4,059,583
[45] Nov. 22, 1977

[54] SUBSTITUTED INDOLES

[75] Inventors: David Fred McComsey, Philadelphia; Michael John Zelesko, Warminster, both of Pa.

[73] Assignee: McNeil Laboratories, Incorporated, Fort Washington, Pa.

[21] Appl. No.: 731,866

[22] Filed: Oct. 13, 1976

Related U.S. Application Data

[63] Continuation-in-part of Ser. No. 631,798, Nov. 13, 1975, abandoned, which is a continuation-in-part of Ser. No. 537,612, Dec. 30, 1974, abandoned.

[51] Int. Cl.$^2$ .......................................... C07D 209/30
[52] U.S. Cl. .................. 260/256.5 R; 260/250 B; 260/288 CE; 260/293.61; 260/294.8 C; 260/302 D; 260/302 H; 260/307 R; 260/308 R; 260/326.12 R; 548/301; 548/336; 548/374; 424/250; 424/251; 424/258; 424/263; 424/267; 424/270; 424/272; 424/273 R; 424/274
[58] Field of Search ............ 260/293.61, 309.6, 309.7, 260/326.12 R, 256.5 R, 250 B, 288 CE, 294.8 C, 302 D, 302 H, 308 R, 309 R, 310 R

[56] References Cited
U.S. PATENT DOCUMENTS
3,285,908   11/1966   Shen ...................................... 260/211

Primary Examiner—Bernard Helfin
Assistant Examiner—Michael Shippen
Attorney, Agent, or Firm—Geoffrey G. Dellenbaugh

[57] ABSTRACT

Substituted thioindoles and their sulfoxide and sulfone derivatives, useful as cardiac rate lowering agents and for other pharmacological properties, and precursors therefor.

35 Claims, No Drawings

SUBSTITUTED INDOLES

CROSS REFERENCE TO RELATED APPLICATIONS

This application is a continuation-in-part of our copending application Ser. No. 631,798, filed Nov. 13, 1975, now abandoned which in turn is a continuation-in-part of application Ser. No. 537,612, filed Dec. 30, 1974, now abandoned.

DESCRIPTION OF THE INVENTION

This invention relates to novel substituted thio-, sulfinyl-, and sulfonylindoles, and more particularly to compounds having the following formulas:

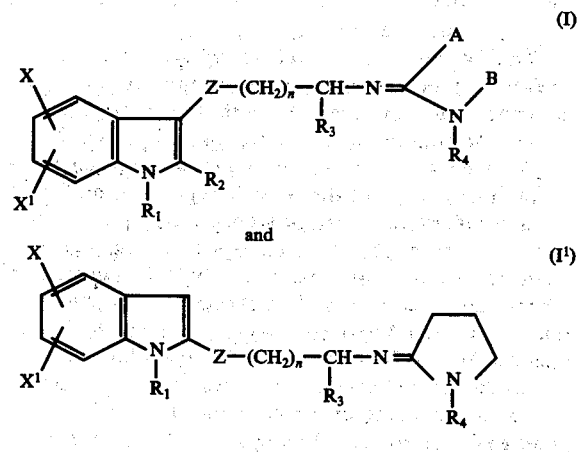

wherein;

X and $X^1$ are each members selected from the group consisting of hydrogen, loweralkyl, loweralkoxy, halo, loweralkylamino and acylamino; provided that X and $X^1$ are not both acylamino; $R_1$ is a member selected from the group consisting of hydrogen, loweralkyl, cycloalkyl, phenyl, substituted phenyl, phenylloweralkyl, substituted phenylloweralkyl, lower alkoxyloweralkyl, alkenyl, alkynyl, cycloalkylloweralkyl, cycloalkenyl;

$R_2$ is a member selected from the group consisting of hydrogen, loweralkyl, phenyl, biphenyl, naphthyl, substituted phenyl, heterocyclic aryl, phenylloweralkyl, and substituted phenylloweralkyl;

Z is a member selected from the group consisting of thio, sulfinyl, and sulfonyl;

$n$ is the integer 1, 2, or 3;

$R_3$ is a member selected from the group consisting of hydrogen and loweralkyl;

$R_4$ is a member selected from the group consisting of hydrogen, loweralkyl, phenyl, substituted phenyl, phenylloweralkyl, substituted phenylloweralkyl, cycloalkyl, hydroxyloweralkyl, and alkenyl;

A and B taken individually are each loweralkyl;

A and B taken together is a member selected from the group consisting of —CH$_2$CH(R$_5$)CH$_2$—, —CH$_2$CH$_2$CH(R$_5$)—, —N(R$_6$)CH(R$_5$)—(CH$_2$)$_m$—, —(CH$_2$)$_4$—, and —CH$_2$)$_5$—, said $R_5$ being a member selected from the group consisting of hydrogen, loweralkyl, phenyl, and substituted phenyl, said $R_6$ being a member selected from the group consisting of hydrogen and loweralkyl, and said $m$ being 1 or 2;

provided that when $m$ is 2, $R_5$ is H; and therapeutically active acid addition salts thereof and precursors therefor.

As used herein, "loweralkyl" and "loweralkoxy" mean a straight or branched chain, saturated, aliphatic hydrocarbon containing from one to about five carbon atoms such as, for example, methyl, ethyl, propyl, isopropyl, butyl, pentyl, and the like loweralkyls, and respectively, methoxy, ethoxy, propoxy, isopropoxy, pentoxy, and the like loweralkoxys. As used herein, the term "halo" is generic to fluorine, chlorine, bromine, and iodine.

The term "cycloalkenyl" includes cyclic monounsaturated hydrocarbons having from five to about seven carbon atoms such as, for example, cyclopentenyl, cyclohexenyl, and cycloheptenyl. The term "substituted phenyl" is used herein to include phenyl substituted with from one to three members each selected from the group consisting of loweralkyl, loweralkoxy, and halo. The term "cycloalkyl" means cyclic aliphatic hydrocarbon radicals having from three to about eight carbon atoms such as cyclopropyl, cyclobutyl, cyclopentyl, cyclohexyl, and the like.

Alkenyl groups and alkynyl groups comprise straight and branched chain, unsaturated, aliphatic hydrocarbons containing from two to about five carbon atoms such as, for example, vinyl, allyl, 1-butenyl, 2-butenyl, 2-methylallyl, 3-methyl-2-butenyl, and the like alkenyls and, respectively, propargyl, 2-butynyl, 3-butynyl, and the like alkynyls.

Heterocyclic aryl groups comprise five- to ten-membered heteroaromatics wherein the hetero atoms are one or more thia, aza or oxa atoms. Included are monocyclic heteroaryls comprising five- to six-members having at least one sulfur, nitrogen or oxygen atom as the heteroatom, and bicyclic heteroaryls having up to ten membersand having, as one of the cyclic moieties, a five- to six-membered heteroaromatic ring with at least one sulfur, nitrogen or oxygen atom as the heteroatom. Specific examples of such groups are pyridyl, quinolyl, imidazolyl, pyrazinyl, pyrrolyl, thienyl, furanyl, thiazolyl, thiadiazolyl, pyrazolyl, triazolyl, oxazolyl and pyrimidinyl. The azaheteroxcyclic aryls may be, if so desired, further substituted at the ring carbon and nitrogen atoms. For example, the heterocyclic moiety may be substituted with a lower alkyl, e.g., 6-methyl-2-pyridyl, 4-ethyl-2-pyrimidyl, and the like; or, for example, a 2-pyrrolyl moiety may be alkylated to the corresponding N-alkyl-2-pyrrolyl. Further, the carbon heterocyclic aryl linkage may be at any one of the several carbon atoms of the heterocycle as, for example, at the 2,3, or 4-positions of the pyridyl moiety.

As used herein the term "acyl" includes loweralkyl carboxy radicals having from one to about five carbon atoms such as acetyl, propionyl, butanoyl, and the like, and phenyl and substituted phenyl carboxy radicals such as benzoyl, p-methylbenzoyl, and the like.

The terms "phenylloweralkyl," "substituted phenylloweralkyl," "loweralkoxyloweralkyl," "cycloalkylloweralkyl," and "heterocyclic aryl loweralkyl" as used herein all refer to substitutent groups wherein the attachment is through the loweralkyl portion and all parts of the groups are as previously defined. Thus, "phenylloweralkyl" includes benzyl, phenethyl, phenpropyl, phenbutyl, and phenpentyl, while "substituted phenylloweralkyl" includes all of the above wherein the phenyl moiety is substituted with from one to three members each selected from the group consisting of loweralkyl, loweralkoxy, and halo. In like fashion, "loweralkoxyloweralkyl" includes methoxymethyl, methoxyethyl, methylpropyl, methoxypentyl, ethoxymethyl, ethoxyethyl, ethoxypentyl, pentoxymethyl, pentoxypentyl, and the like, while "cycloalkylloweralkyl" includes cyclopropylmethyl, cyclopropylethyl, cyclopropylpentyl, cyclobutylmethyl, cyclobutylethyl, cyclohexylmethyl, cyclohexylethyl, cyclohexylbutyl, and the like. Furthermore, "heterocyclic aryl loweralkyl" includes monocyclic heteroaryls comprising five to six members having at least one sulfur, nitrogen or oxygen atom as the heteroatom and bicyclic heteroaryls having up to ten members and having, as one of the cyclic moieties, a five- to six-membered heteroaromatic ring with at least one sulfur, nitrogen or oxygen atom as the heteroatom, said monocyclic and bicyclic heteroaryls being attached at the carbon heterocyclic aryl linkage to a loweralkyl bridge. Specific examples of such groups are 2-benzimidazolylmethyl, 1-benzimidazolylmethyl, 2-picolyl, 3-picolyl, 2-thienylmethyl, 2-thienylethyl, 3-thienylmethyl, 4-imidazolylmethyl, 3-benzo[b]thienylmethyl, 3-benzo[b]thienylethyl, 3-indolylmethyl, 3-indolylethyl, 3-indolyl-3-propyl, 3-indolyl-4-butyl, 2-(p-methoxyphenyl)-4-thiazolylmethyl, furylmethyl.

The preferred compounds of the invention are those of formula (I) wherein $R_1$ is other than hydrogen, the more preferred being those wherein $R_1$ is loweralkyl or alkenyl. Still more preferred are such compounds wherein X and $X^1$ are hydrogen, $R_2$ is hydrogen or loweralkyl, $R_3$ is hydrogen, Z is thio, n is 1, $R_4$ is loweralkyl, and A--B is $-(CH_2)_3-$.

The compounds of formula (I) wherein A—B is $NHCH(R_5)(CH_2)_m$ may exist in two tautomeric forms, illustrated by the following:

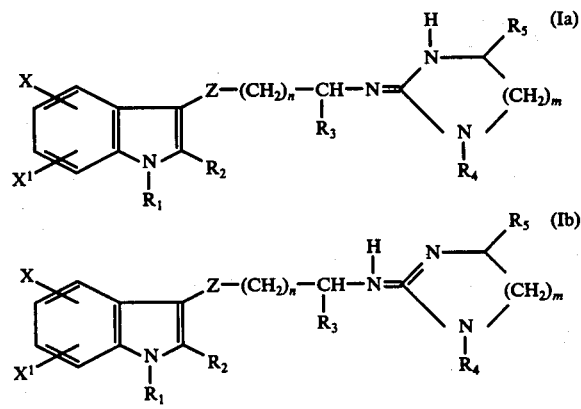

The compounds of formula (I) and (I$^1$) wherein $R_4$ is hydrogen also may each exist in one of two tautomeric forms, illustrated by the following:

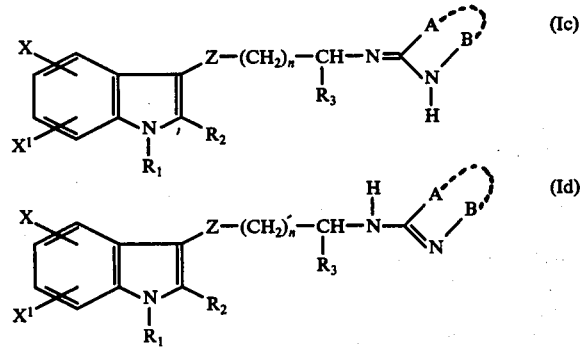

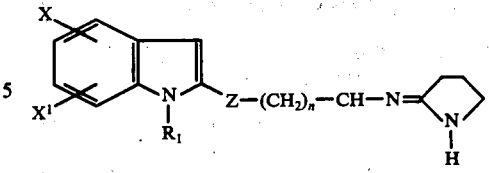

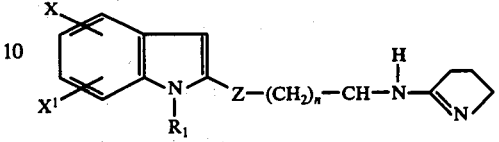

In the above formula X, $X_1$, $R_1$, $R_2$, Z, $R_3$, $R_4$, A, B, and n are as previously defined unless otherewise specified. These tautomeric forms are included within the scope of the present invention.

The compounds of formula (I) wherein Z is thio are preferably prepared by reacting the appropriate fluoroborate salt of formula (II) with the appropriate 3-(aminoalkylthio)indole of formula (III), in which X, $R_1$, $R_2$, $R_3$, $R_4$, A, B, and n are as previously defined. A slight molar excess of the fluoroborate salt is preferred. Suitable organic solvents for conducting the reaction include lower aliphatic alcohols, such as, for example, methanol, ethanol, 2-propanol, tert-butanol and the like; ethers, such as, for example diethylether, tetrahydrofuran, dioxane and the like; lower halogenated hydrocarbons such as chloroform, methylene chloride, 1,2-dichlorethane and the like; and aromatic hydrocarbons such as benzene, toluene, xylene and the like. The temperature is not critical. While ambient temperatures are preferred, elevated temperatures may be employed to increase the rate of reaction. The resulting fluoroborate salt is converted to the corresponding base form by conventional means; for example, by treatment with a suitable base such as an alkali metal or alkaline earth hydroxide, carbonate, and the like. The reaction may be illustrated by the following:

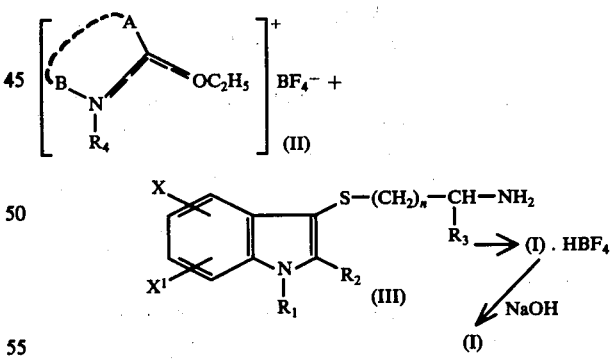

The compounds of formula (I) wherein Z is thio may also be prepared by two other reactions. First, by reacting an appropriate compound of formula (III) with a slight molar excess of an appropriate compound of formula (IV), in which X, $X^1$, $R_1$, $R_2$, $R_3$, $R_4$, $R_5$, A, B, and n are as previously defined and W is a bromo or chloro, to yield compound (I) as its acid salt. This reaction is conducted in a suitable inert organic solvent such as an aromatic hydrocarbon, for example, benzene, toluene, xylene, etc.; an ether, for example, diethyl ether, tetrahydrofuran (THF), dioxane, etc.; a halogenated loweralkane, for example, chloroform, dichloromethane, dichloroethane, etc.; and the like. While temperature is not critical, reflux temperature is preferred. Second, by reacting an appropriate sodium 3-indolylthiolate of formula (V) in aqueous base with a stoichiometric amount of an appropriate compound of formula (VI) in which X, $X^1$, $R_1$, $R_2$, $R_3$, $R_4$, A, B, and n are as previously defined, in a suitable inert organic solvent as previously described. The temperature is not critical. While ambient temperatures are preferred, elevated temperatures may be employed to increase the rate of reaction.

These two reactions may be illustrated by the following:

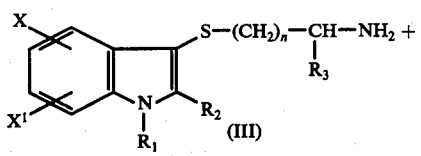

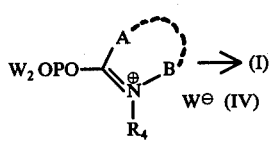

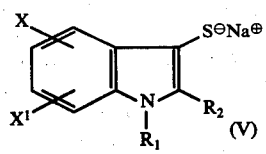

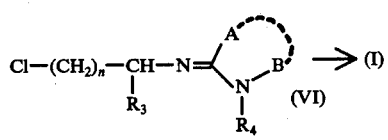

The acid addition salt of the desired product may be converted to the free base (I) as previously described.

The compounds of formula (I) where Z is thio, and A—B is —N($R_6$)CH($R_5$)($CH_2$)$_m$— may also be prepared by reacting an appropriate thioindole of formula (III) with an appropriate alkylthioimidazoline salt or alkylthiotetrahydropyrimidine salt of formula (VII), in which X, $X^1$, $R_1$, $R_2$, $R_3$, $R_4$, $R_5$, $R_6$, and n are as previously described, W is a suitable anion, e.g., from a mineral acid, such as halo, and $R_7$ is loweralkyl. Stoichiometric amounts are preferably employed. This reaction is conducted in an appropriate loweralkanol such as, for example, ethanol, isopropanol, 2-methyl-4-propanol, and the like.

While temperature is not critical, reflux temperature is preferred. This reaction may be illustrated by the following:

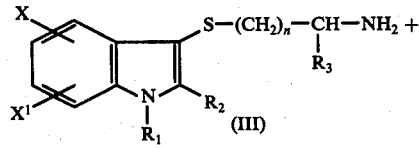

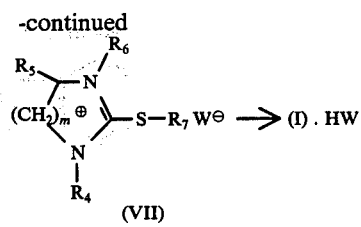

The acid addition salt of the desired product may be converted to the free base (I) as previously described.

The compounds of formula ($I^1$) where Z is thio and $R_3$ is H may be prepared by reacting an appropriate indoline-2-thione of formula (XX) with an appropriate halonitrile of formula (XXI) in a suitable inert organic solvent as previously defined. An excess of the halonitrile is preferred, although equivalent amounts may be used. Ambient temperatures are also preferred, although temperature is not critical. The resulting nitrile of formula (XXII) is then isolated and purified by conventional methods. This 1-unsubstituted nitrile may be 1-substituted in a method completely analogous to that in which the compounds of formula (XVI) are 1-substituted to yield the corresponding substituted nitrile of formula (XXIII).

The nitrile of formula (XXIII) is then reduced with a suitable reducing agent such as borane, lithium aluminum hydride/aluminum chloride, or the like. The reaction is conducted in a suitable inert organic solvent other than a halogenated loweralkane, as previously defined, employing a large molar excess of reducing agent. The temperature is not critical. While ambient temperatures are preferred, elevated temperatures may be employed to increase the rate of reaction. After destruction of the excess reducing agent with mineral acid (borane) or base (lithium aluminum hydride/aluminum chloride), the product amine of formula (XXIV) is obtained as the acid salt or free base, respectively.

This amine may then be reacted with a suitable compound of formula (II) in a fashion identical to the preferred method described above for the preparation of compounds of formula (I) to yield the desired compound of formula ($I^1$).

The indoline-2-thiones are mostly known or may be prepared by the methods of E. H. Wiseman, et al., J. Med. Chem., 16, 131 (1973) and T. Hino, et al., Chem. and Pharm. Bull. (Tokyo), 17, 550 (1969). Throughout the above discussion, X, $X^1$, $R_1$, $R_4$ and n are as previously defined and W is bromo or chloro. The above reactions may be illustrated by the following:

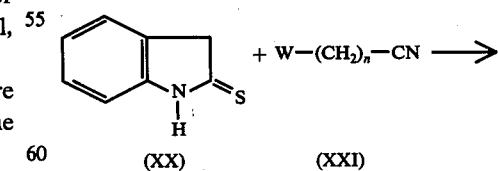

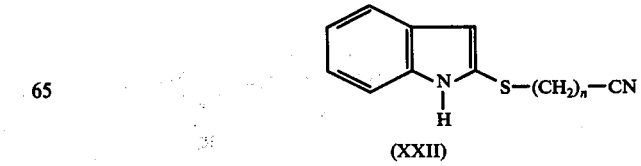

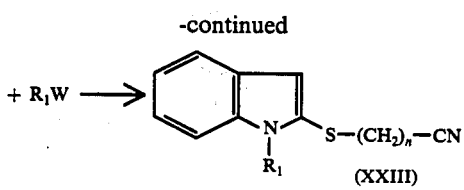

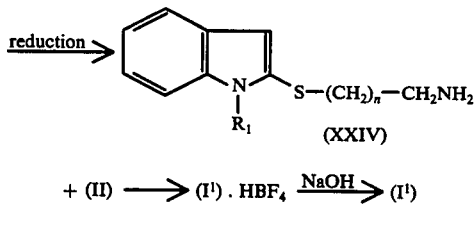

+ (II) ⟶ (I¹) . HBF₄ —NaOH→ (I¹)

The compounds of formula (I¹) where Z is thio and R₃ is not limited to hydrogen may be prepared in an identical fashion as above from compounds of formula (XXIVa), which compounds are generally known or may be prepared by the methods described in, for example, U.S. Pat. No. 3,655,016. This reaction may be illustrated by the following:

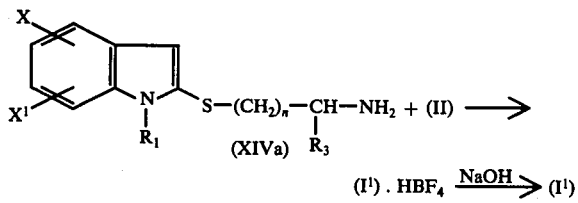

(I¹) . HBF₄ —NaOH→ (I¹)

The compounds of formulas (I) and (I¹) where Z is sulfinyl may be prepared by reacting an appropriate compound of formula (I) where Z is thio with sodium metaperiodate in a suitable organic solvent as previously described. A slight molar excess of sodium metaperiodate is preferably employed. While temperature is not critical, ambient temperatures are preferred. Elevated temperatures may be employed to increase the rate of reaction. This reaction may be illustrated by the following:

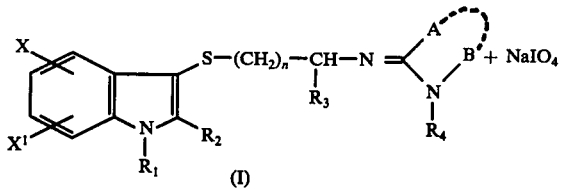

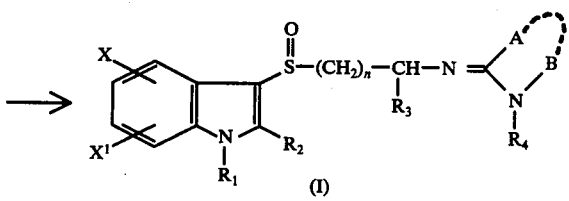

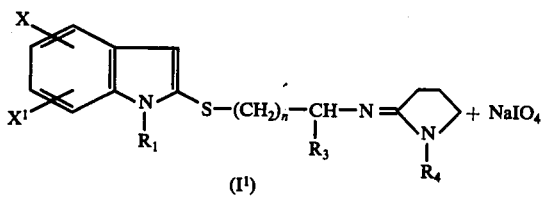

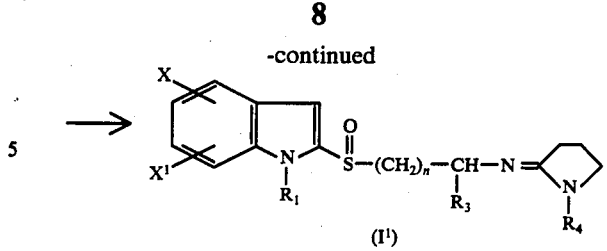

where X, X¹, R₁, R₂, R₃, R₄, A, B, and n are as previously defined.

The compounds of formula (I) and (I¹) wherein Z is SO₂ may be prepared by oxidation of compounds of formula (I) and (I₁), respectively, wherein Z is S or SO. The oxidizing agent, which should be present in excess, is preferably hydrogen peroxide or a peracid. The reaction may be conducted in a suitable organic solvent as previously defined or an organic acid, such as acetic acid, propionic acid, or the like, and preferably at ambient temperatures.

The subject compounds (I) and (I¹) may be isolated as the free bases by synthetic processes normally employed. These compounds in base form are convertible to therapeutically active non-toxic acid addition salts by treatment with an appropriate acid such as, for example, an inorganic acid such as hydrohalic acid, e.g., hydrochloric, hydrobromic or hydroiodic acid; sulfuric or nitric acid; a phosphoric acid; an organic acid such as acetic, propionic, glycolic, lactic, pyruvic, malonic, succinic, maleic, fumeric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicylic, p-aminosalicylic, 2-phenoxybenzoic, or 2-acetoxybenzoic acid. Conversely, the salt form can be converted in the usual manner into the free base.

The subject compounds (I) and (I¹) in free base or acid addition salt form have been found to possess useful cardiac rate lowering activity in mammals by the following reflexogenic tachycardic test. A bilateral vagotomy is performed on the anesthetized dog [anesthesia consists of i.v. administration of thiopental sodium (20 mg/kg) maintained by subsequent i.v. injections of α-chloralose (60 mg/kg)]. Two doses of aminophylline (5 mg/kg i.v.) are administered at 15-minute intervals. The hypotensive effect of aminophylline activates the baroreceptors of the carotid sinus which, in turn, stimulates the sympathetic nervous system causing a reflex rise in the heart rate. Fifteen minutes after the second dose of aminophylline, the compound to be tested is administered i.v. and the effect on the heart rate is noted over a 30-minute period. Compounds showing the heart-rate lowering activity of at least 18 sinus beats per minute for at least 5 minutes are considered to be active. Such compounds are useful in the treatment of angina pectoris, since heart rate is considered to be a major determinant of myocardial oxygen consumption.

The compounds of the invention are active in the above test at dosages ranging from about 0.25 to about 18.5 mg/kg body weight.

The subject compounds (I) and (I¹) in free base or acid addition salt form have also been found to possess useful activity as inhibitors of human platelet aggregation The compounds are tested using collagen-induced aggregation at a final concentration of 100 μM in platelet-rich plasma by the turbidimetric method of Born [G. V. R. Born, Nature, 194, 927 (1962)]. The results are expressed as average percent inhibition of aggregation. While the compounds of the inventions are all active in the above test, the preferred compounds for this utility are those of formula (I) wherein Y is methylene and Z is thio.

The subject compounds of formulas (I) and (I¹) have also been found to possess useful anti-secretory activity by the following acute gastric fistula rat test. The antisecretory activity of the compound to be tested is studied in female Sprague-Dawley rats after intraduodenal (i.d.) injection of the compound at doses generally ranging from 2.5–40 mg/kg body weight. The rats are fasted 24 hours before testing and are given water ad libidum while being kept in individual cages. On the day of testing, the rats are weighed and are selected so that the rats in each test have weights within a range of ±20 g.

Surgery is carried out under light ether anesthesia. As soon as the rat is anesthetized, its teeth are removed, using a small pinch pliers. A mid-line incision is made on the abdomen about 1½ cm in length and the stomach and duodenum are exposed. If at this point the stomach is filled with food or fecal material, the rat is discarded. Using 4-0 suture, a purse string stitch is placed on the fundic portion of the stomach taking care not to pierce any blood vessels in the area. A small nick is made into the stomach in the center of the purse string, and a cannula, consisting of a small vinyl tube with a flange on one end, is put into the stomach and the purse string stitch is closed tightly around the flange. Immediately following this, the test compound is administered i.d. in a volume of 0.5 ml per 100 gm rat. Three rats are generally used for each drug dose tested. Control rats receive the test vehicle, usually 0.5% aqueous methyl cellulose.

After administration of the test compound, the abdominal wall and skin are closed simultaneously with 3 to 4 18 mm wound clips and a collecting tube is placed on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. Volumes are read and a 1 ml aliquot of the supernatant is put into a beaker containing 10 ml distilled H₂O and is titrated to pH7 using 0.01N NaOH. Results are determined for Volume, Titratable Acid, and Total Acid Output where Volume = total ml. of gastric juice minus sediment; Titratable Acid (milliequivalents/1) = amount of 0.01N NaOH needed to titrate the acid to pH7; and Total Acid Output = Titratable Acid X volume. Results are reported in % Inhibition vs. Controls, with 50% inhibition being the criterion for an "active" compound.

Further, certain of the subject compounds (I) in free base or acid addition salt form have been found to possess additional pharmacological activity as described below. Particularly, the compounds (I) wherein Z is thio, $R_1$ contains a cyclic portion (cycloalkyl, phenyl, substituted phenyl, or heterocylic), and A—B is loweralkyl, $CH_2CH(R_5)CH_2$ or $CH_2CH(R_5)CH_2CH_2$ are active as anti-arrhythmia agents and as inhibitors for both epinepherine- and caffeine-stimulated lypolysis, as shown by the following three tests.

Atrial Anti-arrhythmic Test:

The right atrium of an anesthetized dog (anesthesia same as in the reflexogenic sinus tachycardia test) is exposed by right thoracotomy and retraction of the pericardium. Atrial fibrillation, as determined by standard ECG limb led (II), is induced by placing two drops of a 10% solution of acetylocholine on the atrium and then stroking the atrium with a blunt spatula. The period of fibrillation is recorded. Two control periods of fibrillation are produced at 15-minute intervals. The compound to be tested is administered i.v. ten seconds after the next induction. A compound is classified as active if it decreases the period of fibrillation by at least 50%. The certain compounds of formula (I), described above are active at doses from about 1.0 to about 18.5 mg/kg body weight.

Epinephrine Stimulated Lipolysis:

Paired rat epididymal fat pads are incubated in Krebs-Ringer bicarbonate buffer in the presence of 5 μg/ml of epinephrine bitartrate for one hour. Of the paired fat pads, one is used as a control and the compound to be tested is added to the other prior to incubation, such that the final concentration of the test compound is 1.0 mM. The degree of lipolysis is determined by measuring glycerol production by a modification of the double enzyme method of Wieland [Wieland, Biochem Z., 329,313 (1957)].Compounds which inhibit glycerol release at greater than 30% at 1.0 mM or are significant at a 95% confidence limit are considered "active".

Caffeine Stimulated Lipolysis:

Procedure same as above except that caffeine in place of epinephrine is present in the incubation mixture at a concentration of 1.0 mM.

The compounds of formula (III) may be prepared directly by combining an appropriate indole of formula (XVIII) with an appropriate aminoalkylthiol of formula (XIX), in which X, $X^1$, $R_1$, $R_2$, $R_3$, and $n$ are as previously defined, and adding an aqueous solution of iodine or a peroxide (e.g. hydrogen peroxide or sodium peroxide) as an oxidizing agent. Stoichiometric amounts of all three materials are preferred. The reaction is conducted in a suitable lower alkanol as previously defined. The temperature is not critical and elevated temperatures may be employed to increase the rate of the reaction, but ambient temperature is preferred. The reaction is conducted in the absence of air, as for example under a nitrogen atmosphere. After the reaction is complete, the alkanol is evaporated in vacuo, and the product is purified by techniques well known in the art. This reaction may be illustrated by the following:

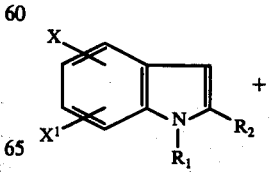

(XVIII)

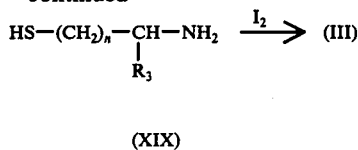

(XIX)

The compounds of formula (III) may also be prepared by one of three other reactions. First, when $n=1$, by reacting an appropriate 3-indolylthiol of formula (VIII) with an appropriate aziridine of formula (IX), in which X, $R_1$, $R_2$, and $R_3$ are as previously defined. The reaction is conducted in a suitable loweralkanol as previously defined. Stoichiometric amounts are preferably employed. Cooling is preferred during mixing of the two reactants, after which the reaction is preferably allowed to proceed at ambient temperature. However, temperature is not critical, and elevated temperatures may be employed to increase the rate of reaction.

Second, when $n$ is 1 or 2, by reacting an appropriate sodium 3-indolylthiolate of formula (V) in aqueous base with an appropriate chloroalkylamine hydrochloride of formula (X), in which X, $R_1$, $R_2$, and $R_3$ are as previously defined. It is preferable that the hydrochloride salt be neutralized by addition of a one molar excess of base or, more preferably, of the 3-indolylthiolate itself. However, stoichiometric amounts may be employed. Ambient temperature is also preferred, but again temperature is not critical and elevated temperatures may be employed to increase the rate of reaction.

Third, when $n$ is 1 or 2 and $R_3$ is H. by reducing an appropriate indol-3-ylthioalkylnitrile of formula (XI), in which X, $X^1$, $R_1$, and $R_2$ are as previously defined. The reducing agent is borane, lithium aluminum hydride/aluminum chloride, or the like. The reaction is conducted in a suitable inert organic solvent as previously defined, employing a large excess of reducing agent. The temperature is not critical. While ambient temperatures are preferred, elevated temperatures may be employed to increase the rate of the reaction. After destruction of the excess reducing agent with mineral acid, (borane) or base (lithium aluminum hydride/aluminum chloride), the product is obtained as the acid salt or free base respectively. These three reactions may be illustrated by the following:

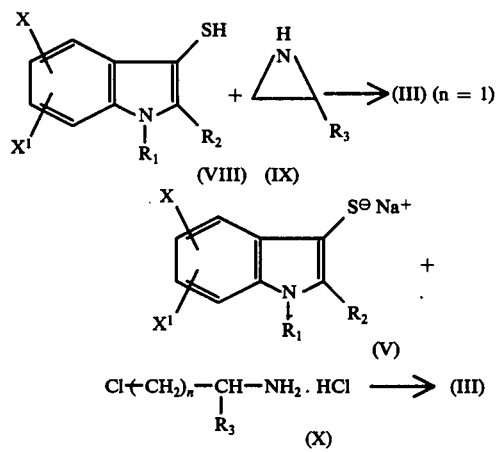

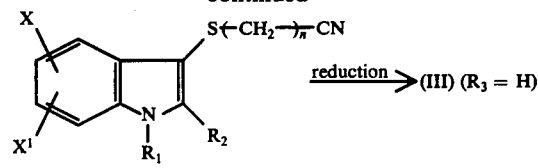

(XI)

The subject compounds (III) may be isolated as the free base by synthetic processess well known in the chemical art. The free bases, in turn, may be converted into therapeutically active, non-toxic, acid addition salts as disclosed above for the compounds of formulas (I) and ($I^1$).

The subject compounds (III) are useful as precursors for the pharmacologically useful compounds of formula (I). Moreover, the compounds of formula (III) themselves possess useful pharmacological properties. They are active as human platelet aggregation inhibitors as shown by the test described above for compounds (I). Further, certain compounds (III) are active in the reflexogenic sinus tachycardia test described above, particularly when $R_1$ is loweralkoxyloweralkyl, phenylalkyl, alkenyl, methyl or isopropyl; and certain Compounds (III) are active in the atrial anti-arrhythmia test described above, particularly when $R_3$ is methyl, when $R_2$ is phenyl, or when $R_1$ is methyl or isopropyl, all other substituents being hydrogen and $n$ being one.

It is believed that certain compounds of formula (III) are novel, particularly those wherein at least one of $R_1$, $R_2$, $R_3$, X and $X^1$ is other than hydrogen or wherein $n$ is two or three. These novel compounds of formula (III) and the therapeutically active acid addition salts thereof are to be considered within the scope of the present invention.

The compounds of formula (II) may be prepared by reacting an appropriate compound of formula (XII), in which A, B, and $R_4$ are as previously defined, with triethyloxonium fluoroborate (XIII), according to the procedure described in Berichte, 89, 2063 (1956). The reaction is conducted in a suitable organic solvent as previously defined, preferably at ambient temperature. This reaction may be illustrated by the following:

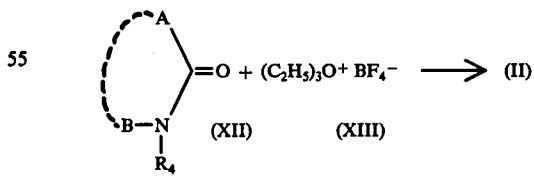

The compounds of formula (IV) may be prepared reacting the appropriate compound of formula (XII), in which A, B, and $R_4$ are as previously defined, with phosphorous oxychloride in benzene according to the procedure described by Brederick, et al., Berichte, 94, 2278 (1961). This reaction may be illustrated by the following:

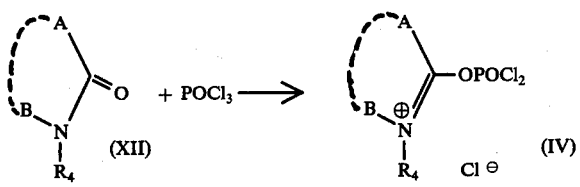

The compounds of formula (V) may be prepared by reacting an appropriate compound of formula (VIII), wherein X, X¹, R₁ and R₂ are as previously defined, with an aqueous solution of NaOH. Both this reaction and the preparation of compound (VIII) have been described by R. L. N. Harris, Tetrahedron Letters, 4465 (1969). Precursors for compound (VIII) can be made by the procedure of C. E. Blades and A. L. Wilds, Journal of Organic Chemistry, 21, 1013 (1956).

The compounds of formula (V) may also be prepared by reaction of appropriate indole of formula (XVIII) with thiourea in the presence of an oxidizing agent. Stoichiometric amounts of the indole, thiourea, and oxidizing agent are preferred. The oxidizing agent may be, for example, iodine/potassium iodide, hydrogen peroxide, potassium periodate, sodium hypochlorite, or the like. The reaction temperature may be ambient or elevated, up to reflux. The solvent may be water, a loweralkanol, an ether (e.g. diethylether, tetrahydrofuran, etc.), a glycol, or the like. When reaction is complete, treatment of the resulting product with concentrated strong base (e.g., aqueous sodium hydroxide), preferably with heating, yields the compound (V).

The compounds of formula (VI) may be prepared by reacting the appropriate compound of formula (XIV), in which $R_3$, $R_4$, A and B, are as previously defined, with thionyl chloride. The reaction is conducted in an appropriate inert organic solvent as previously defined and in the absence of oxygen. A large excess of thionyl chloride is preferably employed. While the materials are preferably cooled to about 0° during mixing, elevated temperatures may be employed during the reaction. The mixture is preferably stirred at ambient conditions and finally refluxed. This reaction may be illustrated by the following:

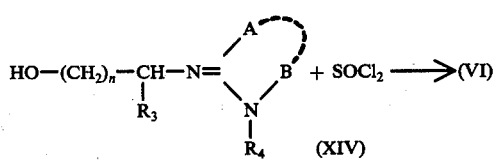

The compounds of formula (XI) may be prepared by reacting the appropriate N-unsubstituted compound of formula (XVI) in a suitable inert organic solvent as previously defined with an appropriate halide R₁W mixed with aqueous base, in which X, X¹, R₁, and R₂ are as previously defined and W is halo, preferably iodide, in the presence of benzyltriethylammonium chloride. A one molar excess of the alkyl halide is preferably employed, but stoichiometric amounts may be used. The reaction is preferably conducted at ambient temperatures and may be illustrated by the following:

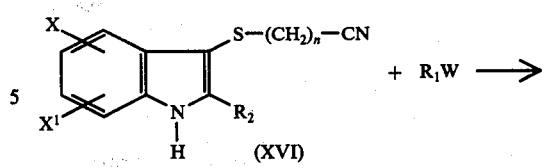

The 1-substituted products of formulas (I) and (I¹) may also be prepared by reacting the 1-unsubstituted (R₁=H) compounds of formulas (I) and (I¹), respectively, with a strong base and then with the appropriate halide, R₁W, all in a suitable inert organic solvent as previously defined. Suitable strong bases are, for example, sodium hydride, lithium hydride, sodamide, and the like, with which the unsubstituted compound (I) or (I¹) is preferably mixed slowly. In the halide, W is preferably iodide or bromide, although chloride may also be used. The desired product is isolated and purified by standard techniques.

This reaction may be illustrated by the following:

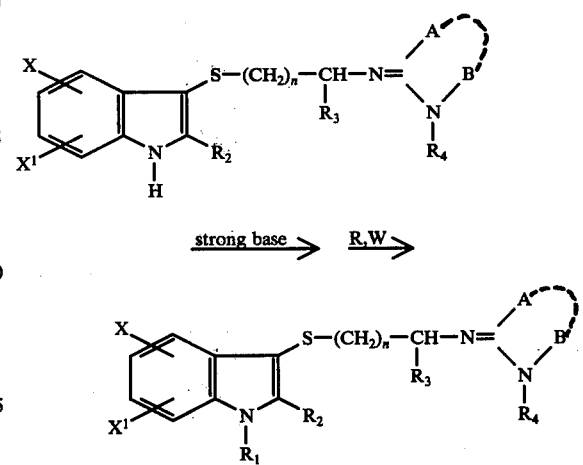

The compounds of formula (XIV) may be prepared by reacting the appropriate compound of formula (II) with the appropriate aminoalkanol of formula (XV), in which A, B, and n, and m are as previously defined. The reaction is conducted in a suitable organic solvent as previously defined. Stoichiometric amounts are preferably employed. The temperature is not critical and elevated temperatures may be employed, but ambient temperature is preferred. The reaction may be illustrated by the following:

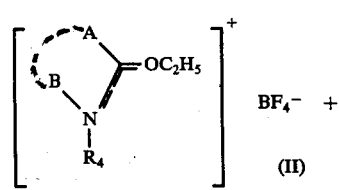

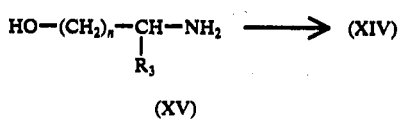

(XV)

The compounds of formula (XVI) may be prepared by reacting the appropriate compound of formula (V) in a suitable inert organic solvent as previously defined with the appropriate haloalkylnitrile of formula (XVII) mixed with aqueous base, in which X, $X^1$, $R_2$, and $n$ are as previously defined. Stoichiometric amounts are preferably employed. Ambient temperatures are preferred, although temperature is not critical. Elevated temperatures may be employed to increase the rate of the reaction. The reaction may be illustrated by the following:

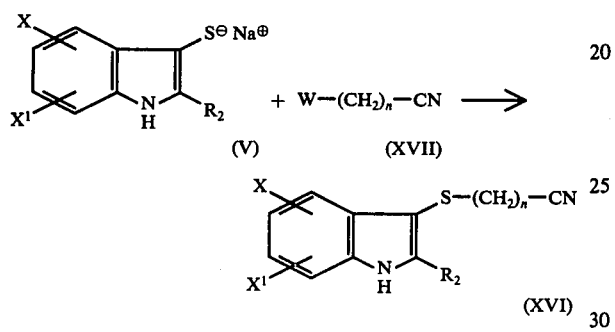

The compounds of formulas (VII), (VIII), (IX), (X), (XII), (XV), (XVII), (XVIII), (XIX), and (XXI) are mostly known and can be prepared by methods well known in the chemical art.

The following examples are intended to illustrate, but not to limit, the scope of the present invention.

EXAMPLE I

3-Indolylthiol: To 240 parts of methanol is added 23.4 parts of indole, 15.2 parts of thiourea, and a sufficient amount of a 1 N aqueous solution of potassium iodide and iodine so that an equivalent of each is present for each equivalent of indole. The whole is stirred for sixteen hours, after which time the solvent is evaporated in vacuo to yield S[3-indolyl]isothiuronium iodide as colorless crystals; m.p. 214°–216°. Treatment of this product with an excess of a concentrated aqueous solution of sodium hydroxide under a nitrogen atmosphere at 80° for ten minutes, followed by cooling to room temperature yields a basic solution of 3-indolylthiol. Neutralization thereof with dilute hydrochloric acid yields as pure product, 3-indolylthiol; m.p. 100°–101°.

EXAMPLE II

Following the procedure of Example I but substituting an equivalent amount of the appropriately substituted indole for the indole used therein, the following substituted 3-indolylthiols are prepared:

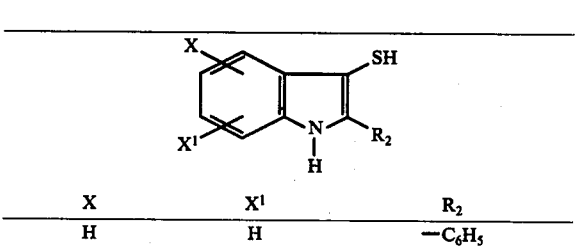

| X | $X^1$ | $R_2$ |
|---|---|---|
| H | H | $-C_6H_5$ |

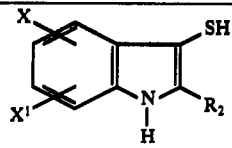

| X | $X^1$ | $R_2$ |
|---|---|---|
| 5-$CH_3O-$ | H | H |
| H | H | $-CH_3$ |
| 5-Cl | H | H |
| 5-$C_2H_5$ | H | H |
| H | H | ![3-methyl-4-chlorophenyl] |
| H | H | ![4-ethoxyphenyl] |
| H | H | ![3-methoxy-4-chloro-6-chlorophenyl] |
| H | H | $-CH_2C_6H_5$ |
| H | H | $-CH_2$-![4-chlorophenyl] |
| 5-$OCH_3$ | 6-$OCH_3$ | H |
| 5-Br | H | H |
| 7-$CH_3$ | H | H |
| H | H | 3-thiazolyl |
| H | H | 2-pyridyl |
| H | H | 3-pyrrolyl |

If desired, the substituted or unsubstituted 3-indoylthiol may be left in solution as sodium 3-indolythiolate by omitting the final cooling and neutralization, and this solution as is in subsequent preparations.

EXAMPLE III

3-Indolythioacetonitrile: To the basic solution of 3-indolythiolate produced in Example I is added 12.1 parts of chloroacetonitrile with about 70 parts of diethyl ether. The whole is stirred under nitrogen for about sixteen hours, after which the ether layer is separated. The aqueous layer is extracted with about 400 parts of dichloromethane and then about 140 parts of diethyl ether. The combined organic fractions are washed with dilute sodium hydroxide and dried over magnesium sulfate, after which the solvent is evaporated in vacuo to leave a brown crystalline solid. Recrystallization of this solid from methanol/isopropanol yields 3-indolyl-thioacetonitrile; m.p. 52°–54.5°.

EXAMPLE IV

Following the procedure of Example III, but substituting equivalent solutions of the substituted sodium 3-indolythiolates of Example II for the unsubstituted sodium 3-indolythiolate solution used therein, the following substituted 3-indolythioalkylnitriles are prepared:

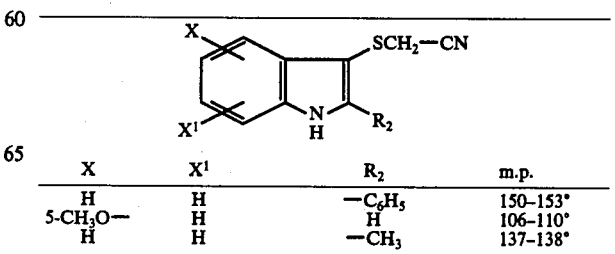

| X | $X^1$ | $R_2$ | m.p. |
|---|---|---|---|
| H | H | $-C_6H_5$ | 150-153° |
| 5-$CH_3O-$ | H | H | 106-110° |
| H | H | $-CH_3$ | 137-138° |

-continued

| X | X¹ | R₂ | m.p. |
|---|---|---|---|
| 5-Cl | H | H | 106–107.5° |
| 5-C₂H₅ | H | H | 61–63° |
| H | H |  | |
| H | H |  | |
| H | H |  | |
| H | H | —CH₂C₆H₅ | |
| H | H |  | |
| 5-OCH₃ | 6-OCH₃ | H | |
| 5-Br | H | H | |
| 7-CH₃ | H | H | |
| H | H | 3-thiazolyl | |
| H | H | 4-pyridyl | |
| H | H | 3-pyrrolyl | |

If desired, the substituted or unsubstituted 3-indolylthioacetonitrile may be kept in solution and used unisolated in subsequent preparations.

EXAMPLE V

1-Methylindol-3-ylthioacetonitrile: The 3-indolylthioacetonitrile from Example III is dissolved in 100 parts of ether and an equal volume of 50% aqueous sodium hydroxide solution is added. To this combination is first added 2 parts of benzyltriethylammonium chloride and then 56.8 parts of methyl iodide with cooling. The container is stoppered and the whole is stirred for about 16 hours. The resulting solution is extracted with 500 parts of diethyl ether and 650 parts of dichloromethane. Each extract is washed twice with dilute aqueous sodium hydroxide solution and once with brine and dried over potassium carbonate. The extracts are then combined and the solvents are evaporated in vacuo to give the crude product, which is recrystallized from methanol-/isopropanol to yield pure 1-methylindol-3-ylthioacetonitrile; mp., 92.5°–93.5° C.

EXAMPLE VI

Following the procedure of Example V, but substituting an equivalent amount of the appropriately substituted 3-indolylthioacetonitrile for the unsubstituted 3-indolylthioacetonitrile used therein and substituting the appropriate iodide for the methyl iodide used therein, the following substituted indol-3-ylthioacetonitriles are prepared:

| X | X¹ | R₁ | R₂ | m.p. |
|---|---|---|---|---|
| H | H | C₂H₅ | H | 37.5–39° C |
| H | H | i-C₃H₇ | H | oil |
| H | H | —CH₃ | —CH₃ | 133–138° C |
| H | H |  | H | oil |
| H | H | —CH₂C₆H₅ | H | oil |
| H | H | —CH₂CH₂OCH₃ | H | oil |
| H | H | —CH₂— | H | oil |
| H | H | -n-C₈H₁₇ | H | oil |
| H | H | —CH₂— | H | |
| H | H | —CH₂CH=CH₂ | H | 45–47° C |
| H | H | —C₆H₅ | H | |
| H | H |  | H | |
| H | H |  | H | |
| H | H | —CH₂——Cl | H | |
| H | H | —CH₂—C≡CH | H | oil |
| H | H | —CH₂C(CH₃)=CH₂ | H | oil |
| 5-OCH₃ | 6-OCH₃ | —C₂H₅ | H | |
| 5-Cl | H | —CH₃ | H | |
| H | H | -n-C₃H₇ | H | |
| H | H | 2-picolyl | H | |
| H | H | 2-thienylmethyl | H | |
| H | H | 3-indolylmethyl | H | |
| H | H | 4-(3-indolyl)butyl | H | |
| H | H | H | 2-thienyl | |
| H | H | H | 4-pyridyl | |
| H | H | CH₃ | 3-thiazolyl | |
| H | H | CH₃ | 3-pyrrolyl | |
| H | H |  | H | |
| H | H | H | 2-pyridyl | |

EXAMPLE VII

3-[(2-Aminoethyl)thio]-1-methylindole fumarate:

To a solution of 45 parts of 1-methylindol-3-ylthioacetonitrile in about 80 parts of tetrahydrofuran (THF) is slowly added with colling 415 parts of 1M borane dissolved in THF. The resulting solution is stirred for about 16 hours protected from moisture, a further 112.5 parts of borane are added, and the whole is stirred for a further sixteen hours. This stirred solution is slowly treated with dilute hydrochloric acid until hydrogen evolution ceases (about six hours) and is then made basic with 1N sodium hydroxide. This basic solution is extracted three times with 150 parts of diethyl ether; the combined extracts are washed three times with dilute sodium hydroxide solution and once with brine and are dried over potassium carbonate. The ethereal solution is evaporated to about half its volume and hydrogen chloride gas is bubbled through it, causing crystallization of the hydrochloride. It is recrystallized from methanol/ethyl acetate to give pure 3-[(2-aminoethyl)thio]-1-methylindole hydrochloride; m.p. 159°–160.5°. The fumarate salt is prepared by concentrating the above ethereal solution before addition of hydrogen chloride gas, and the resulting yellow oil is dissolved in methanol. To this solution is added 9 parts of fumaric acid dissolved in methanol and the solvent is slowly evaporated with the gradual addition of isopropanol. The product which is formed is recrystallized from methanol/isopropanol to yield pure 3-[(2-aminoethyl)-thio]-1-methylindole fumarate; m.p. 169° (dec.).

Calculated for $C_{11}H_{14}N_2S \cdot C_4H_4O_4$: C, 55.88; H, 5.63; N, 8.69.

Found: C, 56.04; H, 5.60; N, 8.57.

EXAMPLE VIII

Following the procedure of example VII, but substituting the appropriately substituted 3-indolylthioacetonitrile for the 1-methylindol-3-ylthioacetonitrile used therein, the following substituted 3-[(2-aminoethyl)thio]-indoles are prepared:

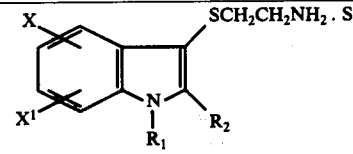

| X | X¹ | R₁ | R₂ | S | m.p. |
|---|---|---|---|---|---|
| H | H | H | H | HCl | 212–215° |
| 5-CH₃O— | H | H | H | HCl | 192–196° |
| H | H | C₂H₅ | H | ½C₄H₄O₄ | 181–182° |
| H | H | i-C₃H₇ | H | C₄H₄O₄ | 176–177.5° |
| H | H | —CH₃ | —CH₃ | HCl | 161–165° |
| H | H | H | —C₆H₅ | — | 125–126.5° |
| 5-Cl | H | H | H | HCl | 245–247.5° (dec) |
| 5-C₂H₅ | H | H | H | HCl | 197–198° |
| H | H | H | CH₃-phenyl-Cl | — | 124–127° |
| H | H | H | phenyl-OC₂H₅ | — | |
| H | H | H | CH₃O, Cl-phenyl-Cl | — | |
| 5-Cl | H | CH₃ | H | | |
| H | H | H | —CH₂C₆H₅ | | |
| H | H | H | —CH₂-phenyl-Cl | | |
| 5-OCH₃ | 6-OCH₃ | H | H | C₄H₄O₄ | 160–161° |
| H | H | cyclopentyl | H | | |
| H | H | —CH₂CH₂OCH₃ | H | C₄H₄O₄ | 147–148° |
| H | H | —CH₂-cyclopropyl | H | ½C₄H₄O₄ | 168–170° |
| H | H | -n-C₈H₁₇ | H | C₄H₄O₄ | 152–153° |
| H | H | —CH₂-furyl | H | C₄H₄O₄ | 166–167° |
| H | H | —C₆H₅ | H | | |
| H | H | phenyl-Cl | H | | |
| H | H | phenyl-(OCH₃)₂ | H | | |
| H | H | —CH₂-phenyl-Cl | H | | |
| H | H | —CH₂—C≡CH | H | C₆H₁₃NO₃S | 136.5–141° |
| 5-Br | H | H | H | | |
| 7CH₃ | H | H | H | | |
| H | H | -n-C₃H₇ | H | ½C₄H₄O₄ | 159.5–160.5° |
| H | H | —CH₂CH=CH₂ | H | C₄H₄O₄ | 158–159° |
| H | H | —CH₂C₆H₅ | H | C₄H₄O₄ | 183–185° |
| H | H | —CH₂C(CH₃)=CH₂ | H | C₄H₄O₄ | 151.5–153° |
| H | H | 2-picolyl | H | | |
| H | H | 2-thienylmethyl | H | | |
| H | H | 3-indolylmethyl | H | | |
| H | H | 3-indolyl-4-butyl | H | | |
| H | H | H | 2-thienyl | | |
| H | H | H | 4-pyridyl | | |
| H | H | CH₃ | 3-thiazolyl | | |

-continued

[Structure: indole with X, X¹ substituents on benzene ring, R₁ on N, R₂ at 2-position, SCH₂CH₂NH₂·S at 3-position]

| X | X¹ | R₁ | R₂ | S m.p. |
|---|----|----|-----|--------|
| H | H | H | 2-pyridyl | |
| H | H | CH₃ | 3-pyrrolyl | |
| H | H | –⟨cyclohexyl⟩ | H | |

EXAMPLE IX 3-(2-Aminopropylthio)indole: To 4.9 parts of the 3-indolylthiol prepared in Example I dissolved in about 24 parts of absolute methanol is added 1.71 parts of propyleneimine. The whole is stirred slowly under nitrogen for about 40 minutes, after which the methanol is evaporated in vacuo and the residue is dissolved in diethyl ether. The ether solution is extracted three times with 50 parts of 1N hydrochloric acid. The combined extracts are washed with about 180 parts of diethyl ether and are then made basic with 2N sodium hydroxide solution. This basic aqueous solution is then extracted three times with 60 parts of diethyl ether; the combined ethereal extracts are washed twice with 50 parts of 1N sodium hydroxide solution and once with brine and are dried over potassium carbonate. The ether is evaporated in vacuo to give the crystalline product, which product is then dissolved in ethyl acetate and activated charcoal is added. After the charcoal is filtered off, scratching of the filtrate yields crude product, which upon recrystallization from benzene yields as pure product, 3-(2-aminopropylthio)-indole; m.p. 110.5° – 112.5° C.

EXAMPLE X

Following the procedure of Example IX, but substituting an equivalent amount of aziridine for the propyleneimine used therein, the following product is obtained:

3-[(2-aminoethyl)thio]indole; m.p. 87°–89° C.

EXAMPLE XI

3-[(3-Aminopropyl)thio]indole: To a basic aqueous solution of 3-indolylthiol produced from 63.8 parts of 3-indolylthiuronium iodide as in Example I is added an aqueous solution of 13.0 parts of 3-chloropropylamine hydrochloride dropwise with stirring. The whole is then stirred for about 3 hours under nitrogen, after which the solution is extracted with about 280 parts of diethyl ether. This ether extract is washed three times with about 150 parts of 1N sodium hydroxide solution and once with brine, and is dried over potassium carbonate. The ether is evaporated to give an oil which crystallized on standing to yield crystalline product. This product is recrystallized from ethyl acetate and is then recrystallized from benzene to which a small amount of activated charcoal has been added to yield pure crystalline 3-[(3-aminopropyl)thio]-indole; m.p. 72.5°–73.5°.

Calculated for $C_{11}H_{14}N_2S$: C, 64.03; H, 6.84. Found: C, 64.02; H, 6.84.

EXAMPLE XII

3-[2-(1-Methyl-2-imadazolinylamino)ethylthio]indole fumarate: A solution of 25.8 parts of 1-methyl-2-methylthio-2-imidazoline hydrochloride and 19.2 parts of 3-[(2-aminoethyl)thio]indole prepared by the procedure of Example IX in 160 parts of 2-propanol is refluxed for 18 hours while protected from light. The yellow oil remaining after the evaporation of the isopropanol in vacuo is treated with 90 parts of 2N sodium hydroxide solution, and the whole is extracted with 400 parts of dichloromethane. The extract is washed twice with dilute sodium hydroxide solution and once with brine, and is dried over potassium carbonate. Evaporation of the dichloromethane in vacuo yields the crude crystalline 3-[2-(1-methyl-2-imadazolinylamino)ethylthio]indole, which is then converted to the fumarate salt by dissolving it in hot methanol and adding 10.8 parts of fumaric acid dissolved in methanol. The fumarate salt is crystallized from solution by addition of isopropanol and cooling and is twice recrystallized from methanol/isopropanol to yield 3-[2-(1-methyl-2-imadazolinylamino)ethylthio]indole fumarate; m.p. 198.5° (dec.).

Calculated for $C_{14}H_{18}N_4S \cdot C_4H_4O_4$ C, 55.37; H, 5.68; N, 14.35 Found: C, 55.33; H, 5.75; N, 14.25

EXAMPLE XIII

Following the procedure of Example XII, but substituting equivalent amounts of the appropriate alkylthioimidazoline and the appropriate 3-[aminoalkylthio]indole for the 1-methyl-2-methylthio-2-imidazoline hydrochloride and 3-[(2-aminoethyl)thio]indole used therein yields the following respective products:

[Structure: indole with X, X¹ on benzene ring, R₁ on N, R₂ at 2-position, S–(CH₂)ₙ–CH(R₃)–N= connected to imidazoline ring with R₄, R₅, R₆ substituents]

| X | X¹ | R₁ | R₂ | n | R₃ | R₄ | R₅ | R₆ |
|---|----|----|----|---|----|----|----|----|
| 5-CH₃O | H | H | H | 1 | H | CH₃ | H | H |
| H | H | H | H | 1 | H | CH₃ | H | CH₃ |
| H | H | H | H | 2 | H | CH₃ | C₆H₅ | H |
| 5-Cl | H | CH₃ | H | 1 | CH₃ | CH₃ | H | C₂H₅ |

EXAMPLE XIV

O-Ethyl-N-methylpyrrolidonium fluoroborate: To a solution of 7.76 parts of epichlorohydrin in 14 parts of anhydrous diethyl ether is slowly added a solution of 15.9 parts of boron trifluoride etherate in 14 parts of anhydrous diethyl ether and the whole is stirred protected from moisture for 3½ hours. The ether is decanted from the resulting solid triethyloxonium tetrafluoroborate, which is washed twice with anhydrous ether and then dried under a stream of nitrogen.

The dried triethyloxonium tetrafluoroborate is dissolved in 26 parts of dry dichloromethane and a solution of 8.32 parts of N-methyl-2-pyrrolidone in 26 parts of dry dichloromethane is added. The whole is stirred for six hours protected from moisture to yield O-ethyl-N-methylpyrrolidonium fluoroborate. While this reagent may be isolated by evaporation of the solvent, it is conveniently used in solution without prior isolation.

EXAMPLE XV

Following the procedure of Example XIV, but substituting an equivalent amount of the appropriate pyrrolidone or piperidone for the N-methyl-2-pyrrolidone used therein yields the following respective products:

| $R_4$ | $R_5$ | m |
|---|---|---|
| H | H | 1 |
| $CH_3$ | $C_6H_5$ | 1 |
| $CH_3$ | H | 2 |
| $CH_3$ | | 1 |
| | 4-$CH_3$-$C_6H_4$- | 1 |
| $CH_3$ | 3,4-$Cl_2$-$C_6H_3$- | 1 |
| $C_2H_5$ | H | 1 |
| —$C_6H_5$ | H | 1 |
| 4-Cl-$C_6H_4$- | H | 1 |
| —$CH_2C_6H_5$ | H | 1 |
| —$CH_2$-(4-Cl-$C_6H_4$) | H | 1 |
| cyclohexyl | H | 1 |
| —$CH_2CH_2OH$ | H | 1 |
| —$CH_2CH$=$CH_2$ | H | 1 |
| —$CH_2C$≡$CH$ | H | 1 |

EXAMPLE XVI

3-[2-(1-Methyl-2-pyrrolidinylideneamino)ethylthio]indole: A suspension of 16.0 parts of 3-[(2-aminoethyl)thio]indole hydrochloride prepared according to Example VII in aqueous base is extracted with 230 parts of benzene. The extract is then washed with 1N sodium hydroxide solution and once with brine, and is dried over potassium carbonate. The benzene is then evaporated in vacuo, and the resulting red oil is dissolved in 60 parts of dry dichloromethane. The resulting solution is added to the solution produced in Example XIV and the whole is stirred for about 18 hours protected from moisture.

The resulting brown solution is extracted twice with 60 parts of 20% sodium hydroxide and is dried over potassium carbonate; the dichloromethane is then evaporated in vacuo to yield the crude free base. This crude free base is recrystallized from isopropanol to yield pure 3-[2-(1-methyl-2-pyrrolidinylideneamino)ethylthio]indole; m.p. 143.5°–145.5° C.

Calculated for $C_{15}H_{19}N_3S$: C, 65.89; H, 7.00; N, 15.37. Found: C, 65.83; H, 6.92; N, 15.37.

EXAMPLE XVII

Following the procedure of Example XVI, but substituting an equivalent amount of an appropriate 3-(aminoalkylthio) indole hydrohalide from Examples VII, VIII, IX, or XXVI for the 3-[(2-aminoethyl)thio]indole hydrochloride used therein, and using an equivalent amount of the appropriate fluoroborate made as in Example XIV or XV, the following respective products are obtained:

3-[3-(1-methyl-2-pyrrolidinylideneamino)propylthio]indole hydrochloride; m.p. 216.5°–218.5° C;

3-[2-(1-methyl-2-pyrrolidinylideneamino)propylthio]indole; m.p. 178.5°–180° C.;

3-[2-(1-methyl-2-pyrrolidinylideneamino)ethylthio]-1-methylindole hemi 2-butenedioate (E); m.p. 186°–189° C.;

5-methoxy-3-[2-(1-methyl-2-pyrrolidinylideneamino)ethylthio]indole; m.p. 154°–157° C. (when ground);

1-ethyl-3-[2-(1-methyl-2-pyrrolidinylideneamino)ethylthio]indole cyclohexanesulfamate; m.p. 113.5°–115.5° C.;

3-[2-(1-methyl-2-pyrrolidinylideneamino)ethylthio]-2-methylindole; m.p. 167°–168.5° C. (when ground);

1,2-dimethyl-3-[2-(1-methyl-2-pyrrolidinylideneamino)ethylthio]indole 2-butenedioate (E); m.p. 149°–150° C;

3-[2-(1-methyl-2-pyrrolidinylideneamino)ethylthio]-2-phenylindole; m.p. 181°–183.5° C.;

5-chloro-3-[2-(1-methyl-2-pyrrolidinylideneamino)ethylthio]indole; m.p. 164.5°–165.5° C.;

3-[2-(1-methyl-4-phenyl-2-pyrrolidinylideneamino)ethylthio]indole; m.p. 162°–163° C.;

3-[2-(1-methyl-2-piperidinylideneamino)ethylthio]indole saccharinate; m.p. 124°–124.5° C.;

3-[2-(2-pyrrolidinylideneamino)ethylthio]indole saccharinate; m.p. 141°–142° C.;

3-[4-(1-methyl-2-pyrrolidinylideneamino)butylthio]indole 2-butenedioate (E); m.p. 172.5°–173.5° C;

1-(1-methylethyl)-3-[2-(1-methyl-2-pyrrolidinylideneamino)-ethylthio]indole; m.p. 82°–84° C;

5-ethyl-3-[2-(1-methyl-2-pyrrolidinylideneamino)ethylthio]-indole; m.p. 131.5°–132.5° C;

2-(3-methyl-5-chlorophenyl)-3-[2-(1-methyl-2-pyrrolidinylideneamino)ethylthio]indole;

2-(4-ethoxyphenyl)-3-[2-(1-methyl-2-pyrrolidinylideneamino)ethylthio]indole;

3-[2-(1-ethyl-2-pyrrolidinylideneamino)ethylthio]-2-(2-methoxy-3,5-dichlorophenyl)indole;

3-[2-(1-methyl-4-p-tolyl-2-pyrrolidinylideneamino)ethylthio]indole;

3-[2-(1-methyl-4-(3,4-dichlorophenyl)-2-pyrrolidinylideneamino)ethylthio]indole;

3-[2-(1-methyl-2-pyrrolidinylideneamino)ethylthio]-1-benzylindole cyclohexylsulfamate monohydrate; m.p. 133°–134° C;
3-[2-(1-methyl-2-pyrrolidinylideneamino)ethylthio]-1-(2-methoxyethyl)indole cyclohexylsulfamate; m.p. 107.5°–109° C;
1-cyclopentyl-3-[2-(1-methyl)-2-pyrrolidinylideneamino)ethylthio]indole benzoate; m.p. 108.5°–110° C;
1-(2-furanylmethyl)-3-[2-(1-methyl-2-pyrrolidinylideneamino)ethylthio]indole 2-butenedioate (E); m.p. 167°–168.5° C;
1-cyclopropylmethyl-3-[2-(1-methyl-2-pyrrolidinylideneamino)ethylthio]indole 2-butenedioate (E); m.p. 133°–134° C;
3-[2-(1-methyl-2-pyrrolidinylideneamino)ethylthio]-1-(2-propenyl)indole cyclohexylsulfamate; m.p. 105°–107.5° C;
3-[2-(1-methyl-2-pyrrolidinylideneamino)ethylthio]-1-(n-octyl)indole furmarate; m.p. 98°–100° C;
3-[2-(1-methyl-2-pyrrolidinylideneamino)ethylthio]-1-phenylindole cyclohexanesulfamate;
1-(4-chlorophenyl)-3-[2-(1-methyl-pyrrolidinylideneamino)ethylthio]indole benzoate;
1-(4-chlorobenzyl)-3-[2-(1-methyl-2-pyrrolidinylideneamino)ethylthio]indole benzoate;
1-(3,4-dimethoxyphenyl)-3-[2-1-methyl-2-pyrrolidinylideneamino)ethylthio]indole benzoate;
3-[2-(1-methyl-2-pyrrolidinylideneamino)ethylthio]-1-(2-propynyl)indole cyclohexylsulfamate; m.p. 114.5°–115.5° C;
5,6-dimethoxy-3-[2-(1-methyl-2-pyrrolidinylideneamino)ethylthio]indole;
2-benzyl-3-[2-(1-methyl-2-pyrrolidinylideneamino)ethylthio]-indole;
2-(4-chlorobenzyl)-3-[2-(1-methyl-2-pyrrolidinylideneamino)ethylthio]indole;
3-{2-[1-(dimethylamino)ethylideneamino]ethylthio}indole cyclohexanesulfamate; m.p. 174°–176.5° C;
5-bromo-3-[2-(1-methyl-2-pyrrolidinylideneamino)ethylthio]indole;
3-[2-(1-phenyl-2-pyrrolidinylideneamino)ethylthio]indole butenedioate (E); m.p. 122°–124° C;
3-[2-(1-(4-chlorophenyl)-2-pyrrolidinylideneamino)ethylthio]-indole;
3-[2-(1-benzyl-2-pyrrolidinylideneamino)ethylthio]indole;
3-[2-(1-(4-chlorobenzyl)-2-pyrrolidinylideneamino)ethylthio]-indole;
3-[2-(1-cyclopentyl-2-pyrroldinylideneamino)ethylthio]indole;
3-{2-[1-(2-hydroxyethyl)-2-pyrrolidinylideneamino]ethylthio}-indole;
3-{2-[1-(2-propynyl)-2-pyrrolidinylideneamino]-ethylthio}indole;
1-(2-methyl-2-propenyl)-3-[2-(1-methyl-2-pyrrolidinylideneamino)ethylthio]indole; m.p. 126.5°–128° C.
7-methyl-3-[2-(1-methyl-2-pyrrolidinylideneamino)ethylthio]-indole cyclohexylsulfamate; m.p. 152.5°–154.5° C;
3-[2-(1-methyl-2-pyrrolidinylideneamino)ethylthio]-1-propylindole 2-naphthalene sulfonate; m.p. 98.5°–100.5° C.;
3-{2-[1-(2-propenyl)-2-pyrrolidinylideneamino]ethylthio}-indole 2-butenedioate (E); m.p. 115°–117° C.
1-(2-picolyl)-3-[2-(1-methyl-2-pyrrolidinylideneamino)ethylthio]-indole;
3-[2-(1-methyl-2-pyrrolidinylideneamino)ethylthio]-1-(2-thienylmethyl)-indole;
1-(3-indolylmethyl)-3-[2-(1-methyl-2-pyrrolidinylideneamino)ethylthio]indole;
1-[4-(3-indolyl)butyl]-3-[2-(1-methyl-2-pyrrolidinylideneamino)ethylthio]-indole;
3-[2-(2-pyrrolidinylideneamino)ethylthio]-2-(2-thienyl)indole;
2-(4-pyridyl)-3-[2-(2-pyrrolidinylideneamino)-ethylthio]indole;
3-[2-(1-methyl-2-pyrrolidinylideneamino)ethylthio]-2-(3-thiazolyl)indole;
3-[2-(2-pyrrolidinylideneamino)ethylthio]-2-(2-pyridyl)indole;
3-[2-(1-methyl-2-pyrrolidinylideneamino)-ethylthio]-2-(3-pyrrolyl)indole.
3-[2-(2-pyrrolidinylideneamino)ethylthio]-1-cyclohex-2-enyl)indole.

EXAMPLE XVIII

3-[2-(1-Methyl-2-pyrrolidinylideneamino)ethylthio]indole:

To a solution of 23.8 parts of N-methyl-2-pyrrolidinone in 450 parts of dry benzene is added dropwise a solution of 36.7 parts of phosphorous oxychloride in 70 parts of dry benzene. The colorless solution is refluxed under nitrogen for 2 hours. The now yellow solution is cooled to room temperature and a solution of 38.4 parts of 3-[(2-aminoethyl)thio]indole in 90 parts of dry benzene is added dropwise in 20 minutes. The mixture is then refluxed for 4½ hours under nitrogen and is allowed to stand for about 18 hours a room temperature.

The resulting mixture is made alkaline by the addition of 300 parts of water and 120 parts of 50% sodium hydroxide solution and the whole is warmed on a steam bath to complete the decomposition of the oily complex. The benzene layer is separated, and the aqueous layer is extracted twice with ether. The extracts are combined, dried over potassium carbonate, and the ether is evaporated in vacuo to give an oily solid. The material is recrystallized twice from isopropanol-pentane to give 3-[2-(1-methyl-2-pyrrolidinylideneamino)ethylthio]indole; m.p. 143°–144° C.

EXAMPLE XIX

3-[2-(1-Methyl-2-pyrrolidinylideneamino)ethylthio]indole:

To the product of Example XIV is added a solution of 4.27 parts of 2-amino-ethanol in 260 parts of dichloromethane, and the whole is stirred at ambient temperature for sixteen hours. The solvent is then evaporated to yield the crude product as the fluoroborate salt. The fluoroborate salt is converted into the free base, which in turn is converted into the perchlorate salt to yield 2-(pyrrolidinylideneamino)ethanol perchlorate; m.p. 67°–69° C.

A solution of 3.5 parts of the above free base in 130 parts of dry chloroform at 0° C. is treated dropwise over a period of 15 minutes under nitrogen with 8.4 parts of thionyl chloride. The whole is then allowed to warm to ambient temperature and is stirred for about sixteen hours. Finally, the whole is refluxed for a half-hour under nitrogen, after which the chloroform and excess thionyl chloride are removed in vacuo to yield the crude product. This residue is dissolved in dichloromethane and the resulting solution is treated with 6N sodium hydroxide solution with vigorous stirring. The dichloromethane layer is separated, dried over potassium carbonate, and filtered. Evaporation of the dichloromethane in vacuo yields the product, 2-(chloroethylimino)pyrrolidine.

A basic solution of 3-indolylthiol is produced from 7.65 parts of 3-indolylthiuronium iodide as in Example I and washed twice with 175 parts of diethyl ether. This aqueous solution is then treated with an ethereal solution of all of the above-prepared 2-(chloroethylimino)-pyrrolidine under nitrogen, and the whole is stirred at ambient temperature for about 16 hours. Dichloromethane is added to replace any ether which evaporated, the organic layer is separated and the aqueous layer is extracted with dichloromethane. The combined organic solutions are dried over potassium carbonate, filtered, and the filtrate evaporated under reduced pressure to yield the product as an amber oil which slowly solidified on scratching. This solid is recrystallized from isopropanol/petroleum ether to yield as pure product, 3-[2-(1-methyl-2-pyrrolidinylideneamino)ethylthio]indole. The infrared spectrum of the pure product is identical to an authentic sample prepared by an alternate route.

EXAMPLE XX

3-[2-(1-Methyl-2-pyrrolidinylideneamino)ethylsulfinyl]indole hemifumarate hydrate:

To a solution of 8.7 parts of 3-[2-(1-methyl-2-pyrrolidinylideneamino)ethylthio]indole in 70 parts of methanol is added 8.2 parts of sodium metaperiodate and 3.5 parts of water with stirring. After the solution has been stirring at ambient temperature for about six hours, the white sodium iodate which has formed is filtered off and washed with methanol. The washing is combined with the filtrate, and the whole is acidified by addition of fumaric acid solution in methanol. Evaporation of the methanol and simultaneous addition of isopropanol yields the crude product. Recrystallization from methanol/acetone yields as pure product, 3-[2-(1-methyl-2-pyrrolidinylideneamino)ethylsulfoxy]indole hemifumarate hydrate; m.p. 154.5°–157.5° C.

EXAMPLE XXI 3-(2-Aminoethyl)thioindole hydrochloride:

To a solution of 1.17 parts of indole and 1.13 parts of 2-aminoethylthiol in 12 parts of methanol is added 11 parts of a 1M aqueous iodine solution slowly under a nitrogen atmosphere and the whole is stirred for one hour. After the methanol has been evaporated in vacuo, the residue is acidified with 2 parts of concentrated hydrochloric acid and the resulting aqueous solution is extracted with diethyl ether. The suspension of aqueous solution and solids is then made basic with sodium hydroxide solution and is further extracted twice with diethyl ether, these combined two extracts then being washed once with brine and dried over potassium carbonate. The ether is then evaporated in vacuo to yield the free base, 3-(2-aminoethyl)thioindole, as an orange oil. Bubbling hydrogen chloride gas through an ether/methanol solution of this oil yields the hydrochloride salt, 3-(2-aminoethyl)thioindole hydrochloride; m.p. 212°–215° C.

EXAMPLE XXII

3-[2-(1-Methyl-2-hexahydroazapinylideneamino)ethylthio]indole 2-butenedioate (E):

A solution of 6.1g. (48 mM) of N-methylcaprolactam in 15 ml of dry $CH_2Cl_2$ is added to a solution of triethyloxonium fluoroborate, prepared from 9.1g (64 mM) of boron trifluoride etherate and 4.45g. (48 mM) of epichlorohydrin, and the whole is stirred under dry conditions for 2½ hours. Then 7.7g (40 mM) of 3-(2-aminoethylthio)indole in 20 ml of dry $CH_2Cl_2$ is added and the solution is stirred under dry conditions at room temperature for 72 hours. An equal volume of $CH_2Cl_2$ is then added and this solution is washed once with 70 ml of 1N NaOH, once with water, and once with brine, and dried over potassium carbonate. The solution is filtered and the filtrate evaporated in vacuo to give 8.6g of orange oily product, which solidified. Purification of the product as the fumarate salt gives 3-[2-(1-Methyl-2-hexahydroazapinylideneamino)ethylthio]indole 2-butenedioate (E) as white crystals; m.p. 128°–130° C.

EXAMPLE XXIII

3-[2-(1-Methyl-1,4,5,6-tetrahydropyrimidin-2-ylideneamino)ethylthio]indole 2-butenedioate (E):

To a solution of 18.9g (75.3 mM) of 1-[2-(indol-2-ylthio)ethyl]thiourea in 80 ml of acetone is added 10.8g of iodomethane, and the reaction mixture is stirred at room temperature protected from moisture for 3½ hours. The acetone is evaporated in vacuo to give an orange oil. To a solution of 13.5g (35 mM) of this oil in 100 ml of dry DMSO is added 3.08g (35 mM) of N-methyl-1-3-propanediamine with stirring and heating. The temperature reached 125° C after 1 hour and 40 minutes and is held there for another hour. The solvent is evaporated in vacuo to give an oily product. This product is dissolved in 50 ml of $CH_2Cl_2$ and treated with 25 ml of water containing 2 ml of concentrated $NH_4OH$ with cooling. The solution is washed once with brine and dried over sodium carbonate. The dried solution is evaporated in vacuo to give 6.0g. of free base as a brown oil.

The fumarate salt is prepared in methanol/isopropanol to yield the product as white-tan crystals; m.p. 212°–213° C.

EXAMPLE XXIV

2-[2-(1-Methyl-2-pyrrolidinylideneamino)ethylthio]indole saccharinate:

To a solution of 25g (188 mM) of oxindole in 500 ml of dry benzene is added 25 g of sand. Then 8.85g (40 mM) of phosphorous pentasulfide is added to the stirred mixture, and the whole is first brought to reflux and held there for 80 minutes and then allowed to cool. The cool reaction mixture is filtered and the solids washed with 300 ml of benzene. The combined filtrate and washings are evaporated in vacuo to give 19.0g (68%) of yellow solid, which is recrystallized from methanol to give 11.6g (41%) of yellow crystalline indoline-2-thione.

To a stirred solution of 26.4g. (0.35 mole) of chloroacetonitrile in 200 ml of pyridine is added 11.0g (74 mM) of the indoline-2-thione. After 1 hour the pyridine hydrochloride is filtered off, and the filtrate is evaporated in vacuo to give an orange oily product. Any remaining pyridine is removed as an azeotrope with water. The oil is extracted into an ether/water mixture, which is washed twice with brine and dried over magnesium sulfate. The dried solution is evaporated in vacuo to give 13.5g of tan solid which is recrystallized from ethylacetate/cyclohexane to give 10.0g of white crystalline indol-2-ylthioacetonitrile; m.p. 91.5°–92.5° C.

To a solution of 6.9g (52 mM) of AlCl₃ and 1.98g (52 mM) of lithium aluminum hydride in 257 ml of anhydrous ether is added 9.8g (52 mM) of this nitrile in 50 ml of anhydrous ether, and the whole is stirred for 2 hours at room temperature. A total of 10g of 50% NaOH and 2 ml of water is added to this reaction mixture over a period of 3 hours and the resulting solution is stirred for 16 hours. The ether is separated from the solids and dried over potassium carbonate. The dried solution is evaporated in vacuo to give 5.4g of product. Further extraction of the reaction solids with ether again after addition of 2.5 ml of water and 10g of 50% NaOH yields an organic layer which is then combined with the 5.4g of product and dried over potassium carbonate. The dried solution is filtered and the filtrate evaporated in vacuo to give 9.0g of 2-(2-aminoethylthio)indole. This amine is converted to the hydrochloride salt with ethereal HCl and is recrystallized once from methanol-/isopropanol to give 6.4g of crystalline solid. A solution of 3.0g (15 mM) of 2-(2-aminoethylthio)indole in 30 ml of dry CH₂Cl₂ is added to a solution of fluoroborate salt prepared from 3.42g (24 mM) of boron trifluoride etherate, 1.69g (18 mM) of epichlorohydrin, and 1.80g (18 mM) of N-methyl-2-pyrrolidinone, in 15 ml of dry CH₂Cl₂. The solution is stirred at room temperature under dry conditions for 4 hours, after which it is washed once with 1N NaOH and twice with brine, and dried over potassium carbonate. The dried solution is evaporated in vacuo to give 3.1g of crude product. Purification as the saccharine salt gives 2-[2-(1-methyl-2-pyrrolidinylideneamino)ethylthio]indole saccharinate as cream colored crystals; m.p. 175°–177° C.

Calc. analysis for C₁₅H₁₉N₃S. C₇H₅O₃NS (273.29/456.57): C, C, 57.87; h, 5.30; N, 12.27. Anal. found: C, 57.84; H, 5.39; N, 12.31

EXAMPLE XXV

3-[2-(1-Methyl-5-phenyl-2-pyrrolidinylideneamino)ethylthio]indole cyclohexanesulfamate:

A solution of 6.3g (36 mM) of N-methyl-5-phenyl-2-pyrrolidone in 10 ml of dry CH₂Cl₂ is added to triethyloxonium fluoroborate in 20 ml of dry CH₂Cl₂. This solution is stirred for 3 hours at room temperature under dry conditions. Then 5.75g (30 mM) of 3-(2-aminoethylthio)-indole in 20 ml of dry CH₂Cl₂ is added, and the resulting solution is stirred under dry conditions for 3 days. Then 50 ml of CH₂Cl₂ is added, and the solution is washed once with 50 ml of 1N NaOH, once with water, and once with brine, and dried over potassium carbonate. The dried solution is evaporated in vacuo to yield the free base as a viscous oily product. Purification as the cyclohexanesulfamate salt gives 3-[2-(1-Methyl-5-phenyl-2-pyrrolidinylideneamino)ethylthio]indole cyclohexanesulfamate as white crystals; m.p. 190.5°–191.5° C.

Anal. calc. for C₂₁H₂₃N₃S. C₆H₁₃NO₃S (349.72) C, 61.33; H, 6.86; N, 10.60. Anal. found: C, 61.40; H, 6.89; N, 10.56

EXAMPLE XXVI

Following the procedure of Example II, but substituting an equivalent amount of chlorobutyronitrile for the chloroacetonitrile used therein, there is prepared 3-indolylthiobutyronitrile.

Then, following the procedure of Example VII, but substituting an equivalent amount of the 3-indolylthiobutyronitrile prepared above for the 1-methylindole-3-ylthioacetonitrile used therein, there is prepared 3-[(4-aminobutyl)thio]indole 2-butenedioate (E); m.p. 116.5°–167.5° C.

The above examples have been provided only by way of illustration and not to limit the scope of the present invention, which scope is defined by the appended claims.

What is claimed is:

1. A member selected from the group consisting of a compound having a formula selected from the group consisting of:

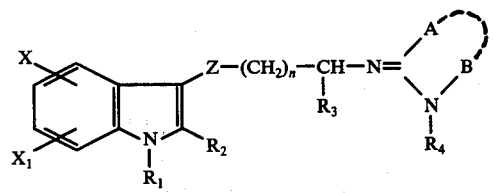

and

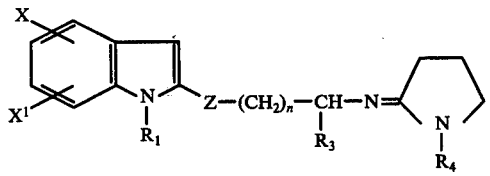

and the therapeutically active acid addition salts thereof, wherein:

X and X¹ are each members selected from the group consisting of hydrogen, loweralkyl, loweralkoxy, halo, loweralkylamino and acylamino; provided that X and X¹ are not both acylamino;

R₁ is a member selected from the group consisting of hydrogen, loweralkyl, cycloalkyl, phenyl, substituted phenyl, phenylloweralkyl, substituted phenylloweralkyl wherein said substitution is on only the phenyl portion, loweralkoxyloweralkyl, alkenyl, alkynyl, cycloalkylloweralkyl, and cycloalkenyl;

R₂ is a member selected from the group consisting of hydrogen, loweralkyl, phenyl, biphenyl, naphthyl, substituted phenyl, heterocyclic aryl, phenylloweralkyl, and substituted phenylloweralkyl wherein said substitution is on only the phenyl portion;

Z is a member selected from the group consisting of thio, sulfinyl, and sulfonyl;

n is the integer 1, 2, or 3;

R₃ is a member selected from the group consisting of hydrogen and loweralkyl;

R₄ is a member selected from the group consisting of hydrogen, loweralkyl, phenyl, substituted phenyl, phenylloweralkyl, substituted phenylloweralkyl wherein said substitution is on only the phenyl portion, cycloalkyl, hydroxyloweralkyl, and alkenyl;

A and B taken individually are each loweralkyl;
A and B taken together is a member selected from the group consisting of —CH$_2$CH(R$_5$)CH$_2$—, —CH$_2$CH$_2$CH(R$_5$)—, —N(R$_6$)CH(R$_5$)(CH$_2$)$_m$—, —(CH$_2$)$_4$—, and —(CH$_2$)$_5$—, said R$_5$ being a member selected from the group consisting of hydrogen, loweralkyl, phenyl, and substituted phenyl, said R$_6$ being a member selected from the group consisting of hydrogen and lower-alkyl, and said $m$ being 1 or 2; provided that when $m$ is 2, R$_5$ is H; said cycloalkyl having from 3 to about 8 carbon atoms, said alkenyl having from 2 to about 5 carbon atoms; said alkynyl having from about 2 to about 5 carbon atoms; said cycloalkenyl having from 5 to about 7 carbon atoms; said cycloalkyl-loweralkyl having from 3 to about 8 carbon atoms in its cycloalkyl portion and from 1 to about 5 carbon atoms in its loweralkyl portion; said acyl consisting of loweralkyl carboxy radicals, phenyl carboxy radicals, and substituted phenyl carboxy radicals; said substituted phenyl being phenyl substituted with from 1 to 3 members each selected from the group consisting of loweralkyl, loweralkoxy, and halo; and said heterocyclic aryl comprising 5- to 10-membered heteroaromatics wherein the hetero atoms are one or more thia, aza or oxa atoms.

2. A member selected from the group consisting of a compound of formula:

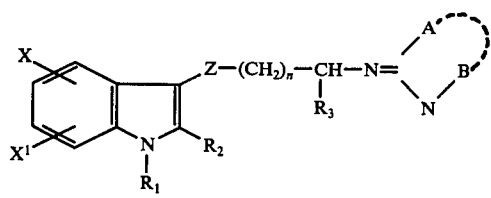

and the therapeutically active acid addition salts thereof, wherein:
X and X$^1$ are each members selected from the group consisting of hydrogen, loweralkyl, loweralkoxy, halo, loweralkylamino and acylamino; provided that X and X$^1$ are not both acylamino;
R$_1$ is a member selected from the group consisting of hydrogen, loweralkyl, cycloalkyl, phenyl, substituted phenyl, phenylloweralkyl, substituted phenylloweralkyl wherein said substitution is on only the phenyl portion, loweralkoxy loweralkyl, alkenyl, alkynyl, cycloalkylloweralkyl, and cycloalkenyl;
R$_2$ is a member selected from the group consisting of hydrogen, loweralkyl, phenyl, biphenyl, naphthyl, substituted phenyl, heterocyclic aryl, phenylloweralkyl, and substituted phenylloweralkyl wherein said substitution is on only the phenyl portion;
Z is a member selected from the group consisting of thio, sulfinyl, and sulfonyl;
$n$ is the integer 1, 2, or 3;
R$_3$ is a member selected from the group consisting of hydrogen and loweralkyl;
R$_4$ is a member selected from the group consisting of hydrogen, loweralkyl, phenyl, substituted phenyl, phenylloweralkyl, substituted phenylloweralkyl wherein said substitution is on only the phenyl portion, cycloalkyl, hydroxyloweralkyl, alkenyl, and alkynyl;

A and B taken individually are each loweralkyl;
A and B taken together is a member selected from the group consisting of —CH$_2$CH(R$_5$)CH$_2$—, —CH$_2$CH$_2$CH(R$_5$), —N(R$_6$)CH(R$_5$)(CH$_2$)$_m$—, —(CH$_2$)$_4$—, and —(CH$_2$)$_5$—, said R$_5$ being a member selected from the group consisting of hydrogen, phenyl, and substituted phenyl, said R$_6$ being a member selected from the group consisting of hydrogen and loweralkyl, said $m$ being 1 or 2; provided that when $n$ is 2, R$_5$ is H;
said cycloalkyl having from 3 to about 8 carbon atoms, said alkenyl having from 2 to about 5 carbon atoms, said alkynyl having from about 2 to about 5 carbon atoms; said cycloalkenyl having from 5 to about 7 carbon atoms; said cycloalkylloweralkyl having from 3 to about 8 carbon atoms in its cycloalkyl portion and from 1 to about 5 carbon atoms in its loweralkyl portion; said acyl consisting of loweralkyl carboxy radicals; phenyl carboxy radicals, and substituted phenyl carboxy radicals; said substituted phenyl being phenyl substituted with from 1 to 3 members each selected from the group consisting of loweralkyl, loweralkoxy, and halo; and said heterocyclic aryl comprising 5- to 10-membered heteroaromatics wherein the hetero atoms are 1 or more thia, aza or oxa atoms.

3. A member selected from the group consisting of 3-[2-(1-methyl-2-pyrrolidinylideneamino)ethylthio]indole and the therapeutically active acid addition salts thereof.

4. A member selected from the group consisting of 3-[3-(1-methyl-2-pyrrolidinylideneamino)propylthio]indole and the therapeutically active acid addition salts thereof.

5. A member selected from the group consisting of 3-[2-(1-methyl-2-pyrrolidinylideneamino)propylthio]indole and the therapeutically active acid addition salts thereof.

6. A member selected from the group consisting of 3-[2-(1-methyl-2-pyrrolidinylideneamino)ethylthio]-1-methylindole and the therapeutically active acid addition salts thereof.

7. A member selected from the group consisting of 5-methoxy-3-[2-(1-methyl-2-pyrrolidinylideneamino)ethylthio]indole and the therapeutically active acid addition salts thereof.

8. A member selected from the group consisting of 1-ethyl-3-[2-(1-methyl-2-pyrrolidinylideneamino)ethylthio]indole and the therapeutically active acid addition salts thereof.

9. A member selected from the group consisting of 3-[2-(1-methyl-2-pyrrolidinylideneamino)ethylthio]-2-methylindole and the therapeutically active acid addition salts thereof.

10. A member selected from the group consisting of 1,2-dimethyl-3-[2-(1-methyl-2-pyrrolidinylideneamino)ethylthio]indole and the therapeutically active acid addition salts thereof.

11. A member selected from the group consisting of 3-[2-(1-methyl-2-pyrrolidinylideneamino)ethylthio]-2-phenylindole and the therapeutically active acid addition salts thereof.

12. A member selected from the group consisting of 3-[2-(1-methyl-2-imidazolinylamino)ethylthio]indole and the therapeutically active acid addition salts thereof.

13. A member selected from the group consisting of 3-[2-(1-methyl-2-pyrrolidinylideneamino)ethylsulfinyl]- indole and the therapeutically active acid addition salts thereof.

14. A member selected from the group consisting of 3-[2-(1-methyl-2-pyrrolidinylideneamino]ethylthio]-1-benzylindole and the therapeutically active acid addition salts thereof.

15. A member selected from the group consisting of 3-[2-(1-methyl-2-pyrrolidinylideneamino)ethylthio]-1-(2-methoxyethyl)indole and the therapeutically active acid addition salts thereof.

16. A member selected from the group consisting of 1-cyclopentyl-3-[2-(1-methyl-2-pyrrolidinylideneamino)ethylthio]indole and the therapeutically active acid addition salts thereof.

17. A member selected from the group consisting of 1-(2-furanylmethyl)-3-[2-(1-methyl-2-pyrrolidinylideneamino)ethylthio]indole and the therapeutically active acid addition salts thereof.

18. A member selected from the group consisting of 1-(cyclopropylmethyl)-3-[2-(1-methyl-2-pyrrolidinylideneamino)ethylthio]indole and the therapeutically active acid addition salts thereof.

19. A member selected from the group consisting of 3-[2-(1-methyl-2-pyrrolidinylideneamino)ethylthio]-1-(2-propenyl)indole and the therapeutically active acid addition salts thereof.

20. A member selected from the group consisting of 3-[2-(1-methyl-2-pyrrolidinylideneamino)ethylthio]-1-(n-octyl)indole and the therapeutically active acid addition salts thereof.

21. A member selected from the group consisting of 3-{2-[1-(dimethylamino)ethylideneamino]ethylthio}indole and the therapeutically active acid addition salts thereof.

22. A member selected from the group consisting of 5-ethyl-3-[2-(1-methyl-2-pyrrolidinylideneamino)ethylthio]indole and the therapeutically active acid addition salts thereof.

23. A member selected from the group consisting of 3-[2-(1-methyl-4-phenyl-2-pyrrolidinylideneamino)ethylthio]indole and the therapeutically active acid addition salts thereof.

24. A member selected from the group consisting of 5-chloro-3-[2-(1-methyl-2-pyrrolidinylideneamino)ethylthio]indole and the therapeutically active acid addition salts thereof.

25. A member selected from the group consisting of 1-(1-methylethyl)-3-[2-(1-methyl-2-pyrrolidinylideneamino)ethylthio]indole and the therapeutically active acid addition salts thereof.

26. A member selected from the group consisting of 3-[2-(2-pyrrolidinylideneamino)ethylthio]indole and the therapeutically active acid addition salts thereof.

27. A member selected from the group consisting of 3-[2-(1-methyl-2-piperidinylideneamino)ethylthio]indole and the therapeutically active acid addition salts thereof.

28. A member selected from the group consisting of 3-[4-(1-methyl-2-pyrrolidinyldeneamino)butylthio]indole and the therapeutically active acid addition salts thereof.

29. A member selected from the group consisting of 1-(2-methyl-2-propenyl)-3-[2-(1-methyl-2-pyrrolidinylideneamino)ethylthio]indole and the therapeutically active acid addition salts thereof.

30. A member selected from the group consisting of 3-[2-(1-methyl-2-pyrrolidinylideneamino)ethylthio]-1-propylindole and the therapeutically active acid addition salts thereof.

31. A member selected from the group consisting of 3-{2-[1-(2-propenyl)-2-pyrrolidinylideneamino]ethylthio}indole and the therapeutically active acid addition salts thereof.

32. A member selected from the group consisting of 3-[2-(1-methyl-2-hexahydroazapinylideneamino)ethylthio]indole and the therapeutically active acid addition salts thereof.

33. A member selected from the group consisting of 3-[2-(1-methyl-1,4,5,6-tetrahydropyrimidin-2-ylideneamino)ethylthio]indole and the therapeutically active acid addition salts thereof.

34. A member selected from the group consisting of 2-[2-(1-methyl-2-pyrrolidinylideneamino)ethylthio]indole and the therapeutically active acid addition salts thereof.

35. A member selected from the group consisting of 3-[2-(1-methyl-5-phenyl-2-pyrrolidinylideneamino)ethylthio]indole and the therapeutically active acid addition salts thereof.

* * * * *

UNITED STATES PATENT AND TRADEMARK OFFICE
CERTIFICATE OF CORRECTION

PATENT NO. : 4,059,583

DATED : November 22, 1977

INVENTOR(S) : David Fred McComsey; Michael John Zelesko

It is certified that error appears in the above-identified patent and that said Letters Patent are hereby corrected as shown below:

Column 1, Formula (I'), right portion of formula,

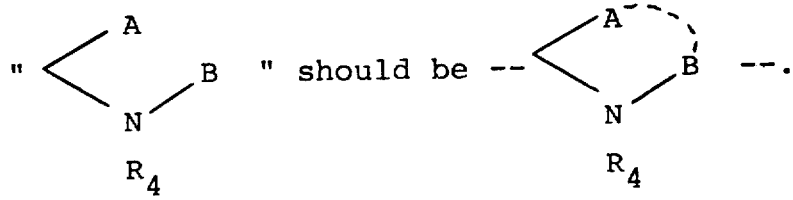

Column 7, Line 32, "(XIVa)" should be -- (XXIVa) --.
Column 8, Line 14, "(I$_1$)" should be -- (I') --.
Column 10, Line 9, "led" should be -- lead --.
Column 16, Line 32 and 33, "3-indoyl-thiol" should be
    -- 3-indolyl-thiol --.
Column 16, Line 33, "3-indolythiolate" should be
    -- 3-indolylthiolate --.
Column 16, Line 37, "3-Indolythioacetonitrile" should be
    -- 3-Indolylthioacetonitrile --.
Column 16, Line 38, "3-indolythiolate" should be
    -- 3-indolylthiolate --.
Column 18, Line 51, "colling" should be -- cooling --.
Column 21, Line 59, "potasium" should be -- potassium --.

UNITED STATES PATENT AND TRADEMARK OFFICE
CERTIFICATE OF CORRECTION

PATENT NO. : 4,059,583

DATED : November 22, 1977

INVENTOR(S) : David Fred McComsey; Michael John Zelesko

It is certified that error appears in the above–identified patent and that said Letters Patent are hereby corrected as shown below:

Column 25, Line 23, "(1-methyl-pyr-" should be
 -- (1-methyl-2-pyr- --.
Column 30, Line 12, "116.5-167.5°C." should be
 -- 166.5-167.5°C. --.

Signed and Sealed this

Seventeenth Day of July 1979

[SEAL]

Attest:

LUTRELLE F. PARKER

Attesting Officer

Acting Commissioner of Patents and Trademarks